(12) United States Patent
Evans

(10) Patent No.: US 7,452,341 B2
(45) Date of Patent: Nov. 18, 2008

(54) SOFT CAST MATERIAL

(75) Inventor: John C. Evans, Nr. Rochdale (GB)

(73) Assignee: BSN Medical, Inc., Charlotte, NC (US)

( * ) Notice: Subject to any disclaimer, the term of this patent is extended or adjusted under 35 U.S.C. 154(b) by 0 days.

(21) Appl. No.: 10/598,424

(22) PCT Filed: Mar. 1, 2004

(86) PCT No.: PCT/US2004/006198

§ 371 (c)(1), (2), (4) Date: Aug. 29, 2006

(87) PCT Pub. No.: WO2005/094246

PCT Pub. Date: Oct. 13, 2005

(65) Prior Publication Data

US 2007/0135744 A1 Jun. 14, 2007

(51) Int. Cl.
*A61F 5/00* (2006.01)

(52) U.S. Cl. .............................................. 602/8; 602/6

(58) Field of Classification Search ..................... 602/5, 602/6, 8
See application file for complete search history.

(56) References Cited

U.S. PATENT DOCUMENTS

| 4,893,617 A | * | 1/1990 | Bartial et al. | 602/8 |
| 4,968,542 A | * | 11/1990 | Gasper et al. | 428/76 |
| 5,007,418 A | * | 4/1991 | Bartizal et al. | 602/9 |

* cited by examiner

*Primary Examiner*—Kim M Lewis
(74) *Attorney, Agent, or Firm*—Adams Intellectual Property Law, P.A.

(57) ABSTRACT

A medical bandaging product, including a package formed of a moisture-impervious material and sealable to prevent entry of moisture. A medical bandage is positioned within the package in substantially moisture-free conditions and sealed therein against moisture until use. The medical bandage is constructed of a fabric having a pair of opposed, major surfaces and a reactive system impregnated into or coated onto the fabric. The reactive system remains stable when maintained in substantially moisture-free conditions and hardens upon exposure to sufficient moisture to form a self-supporting structure having an immobilization value of less than about 43. The fabric is preferably knitted.

22 Claims, 5 Drawing Sheets

US 7,452,341 B2

SOFT CAST MATERIAL

TECHNICAL FIELD AND BACKGROUND OF THE INVENTION

This invention relates to an initially flexible cast material that hardens in the presence of water into a semi-rigid state capable of maintaining a body part, such as an arm or leg, in an orthopedically suitable, stable, treatment orientation while permitting a medically appropriate degree of movement to the cast and enclosed body part.

Conventional moisture-curable bandages incorporate substrates impregnated with plaster-of-paris or formed from flexible fiberglass fabric layers impregnated with a moisture-curable resin. Bandages formed from these materials possess several disadvantages. In particular, casts formed using plaster-of-paris bandages have a relatively low strength to weight ratio. This results in a finished cast that is very heavy and bulky. Furthermore, plaster-of-paris splints are slow to harden, requiring 24 to 72 hours to reach maximum strength. Because plaster-of-paris breaks down in water, bathing and showering are difficult. Even if wetting due to these causes can be avoided, perspiration over an extended period of time can break down the plaster-of-paris and create a significant problem with odor and itching.

Although medical bandages utilizing moisture-curable substrates formed from fiberglass fabric layers are lighter, waterproof and permeable to X-rays, cured casts made using such bandages can become brittle, break down during wear and often need to be replaced. Furthermore, fiberglass is a composition that is highly irritating to mammalian skin. When fiberglass casts are removed, irritating dust or fibers are often generated and become embedded in the skin of the patient.

This invention overcomes the disadvantages of prior art fiberglass substrates by providing a medical bandage formed from a resin-impregnated substrate formed from a knitted fabric that incorporates low modulus, inelastic and elastic fibers. The unique substrate of the present invention results in a bandage that exhibits good conformability compared to prior art fiberglass substrates, possesses sufficient rigidity when cured, and shows no loss of strength compared to casts formed from fiberglass substrates. This novel substrate is less brittle and more durable than prior art fiberglass substrates when cured, and does not disintegrate into irritating dust and/or fibers when removed from the injured body part of a patient.

The material is preferably in the form of an elongate knitted tape that is wrapped around the injured limb or other body part while flexible, and that cures in several minutes to the required degree of rigidity. The term "soft" is used only as a term of degree to distinguish it from known cast tapes that are expressly designed to cure to a very rigid state. The invention described below is designed to cure to a less than fully rigid state, and the term "soft" describes this product in comparison to cast tapes that are designed to cure to a very rigid state.

The invention disclosed and claimed in the invention includes a cast tape that incorporates a fiberglass free fabric knitted from high tenacity polypropylene and polyester yarns. The tape is therefore radiolucent, thus requiring less cast removals during treatment.

As described below, the degree of residual flexibility that imparts the comparatively "soft" characteristics is quantified by the term "Immobilization Value", or "IV."

Prior art soft cast tapes include fiberglass medical bandages disclosed in U.S. Pat. Nos. 4,968,542; 4,893,617; and 5,007,418. These patents disclose fiberglass cast tape having an Immobilization Value of between 45-50 and 400 pounds.

SUMMARY OF THE INVENTION

Therefore, it is an object of the invention to provide an initially-flexible cast material that cures to a semi-rigid state.

It is another object of the invention to provide an initially-flexible cast material that cures to a semi-rigid state and that is completely radiolucent.

It is another object of the invention to provide an initially-flexible cast material that cures to a semi-rigid state and that contains no fiberglass.

It is another object of the invention to provide an initially-flexible cast material that cures to a semi-rigid state and is comprised of high tenacity polypropylene and high tenacity polyester.

It is another object of the invention to provide an initially-flexible cast material that rapidly cures in the presence of water to an Immobilization Value of less than about 43 pounds.

These and other objects of the present invention are achieved in the preferred embodiments disclosed below by providing a medical bandaging product, comprising a package formed of a moisture-impervious material and sealable to prevent entry of moisture and a medical bandage positioned within the package in substantially moisture-free conditions and sealed therein against moisture until use. The medical bandage comprises a fabric having a pair of opposed, major surfaces and a reactive system impregnated into or coated onto the fabric, the system remaining stable when maintained in substantially moisture-free conditions and hardening upon exposure to sufficient moisture to form a self supporting structure having an immobilization value of less than about 43 pounds.

According to one preferred embodiment of the invention, the fabric comprises a knitted fabric.

According to another preferred embodiment of the invention, the fabric comprises a knitted fabric fabricated from high tenacity polyester and high-tenacity polypropylene yarns.

According to yet another preferred embodiment of the invention, the fabric includes an elastic yarn.

According to yet another preferred embodiment of the invention, the medical bandage comprises a rolled elongate tape.

According to yet another preferred embodiment of the invention, the immobilization value of the medical bandage is between about 30 and 43 pounds.

According to yet another preferred embodiment of the invention, the medical bandage is fabricated from high tenacity polypropylene, a high tenacity polyester and an elastic yarn.

According to yet another preferred embodiment of the invention, the high tenacity polypropylene yarn comprises 470 Dtex yarn, the high tenacity polyester yarn comprises 280 Dtex yarn and the elastic yarn comprises 70 Dtex uncovered Elastane.

According to yet another preferred embodiment of the invention, the reactive system comprises a blended polyisocyanate, polyol, catalyst and stabilizer.

According to yet another preferred embodiment of the invention, the polyol comprises a 55 percent by weight polyol blend.

According to yet another preferred embodiment of the invention, the medical bandage has a reactive system add-on of between about 50 and 56 percent by weight.

According to yet another preferred embodiment of the invention, a cast tape is provided and comprises an elongate bandage for being positioned within a package in substantially moisture-free conditions and sealed therein against moisture until use. The cast tape comprises a fabric having a pair of opposed, major surfaces, and a reactive system impregnated into or coated onto the fabric, the system remaining stable when maintained in substantially moisture-free conditions and hardening upon exposure to sufficient moisture to form a self supporting structure having an immobilization value of less than about 43.

According to yet another preferred embodiment of the invention, the fabric comprises a knitted fabric.

According to yet another preferred embodiment of the invention, the fabric comprises a knitted fabric fabricated from high tenacity polyester and high-tenacity polypropylene yarns.

According to yet another preferred embodiment of the invention, the fabric includes an elastic yarn.

According to yet another preferred embodiment of the invention, the cast tape is formed into a roll.

According to yet another preferred embodiment of the invention, the immobilization value of the cast tape is between about 30 and 43 pounds.

According to yet another preferred embodiment of the invention, the cast tape is fabricated from high tenacity polypropylene, high tenacity polyester and an elastic yarn.

According to yet another preferred embodiment of the invention, the high tenacity polypropylene yarn comprises 470 Dtex yarn, the high tenacity polyester yarn comprises 280 Dtex yarn and the elastic yarn comprises 70 Dtex uncovered Elastane.

According to yet another preferred embodiment of the invention, the reactive system comprises a blended polyisocyanate, polyol, catalyst and stabilizer.

According to yet another preferred embodiment of the invention, the polyol comprises a 55 percent by weight polyol blend.

According to yet another preferred embodiment of the invention, the medical bandage has a reactive system add-on of between about 50 and 56 percent by weight.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
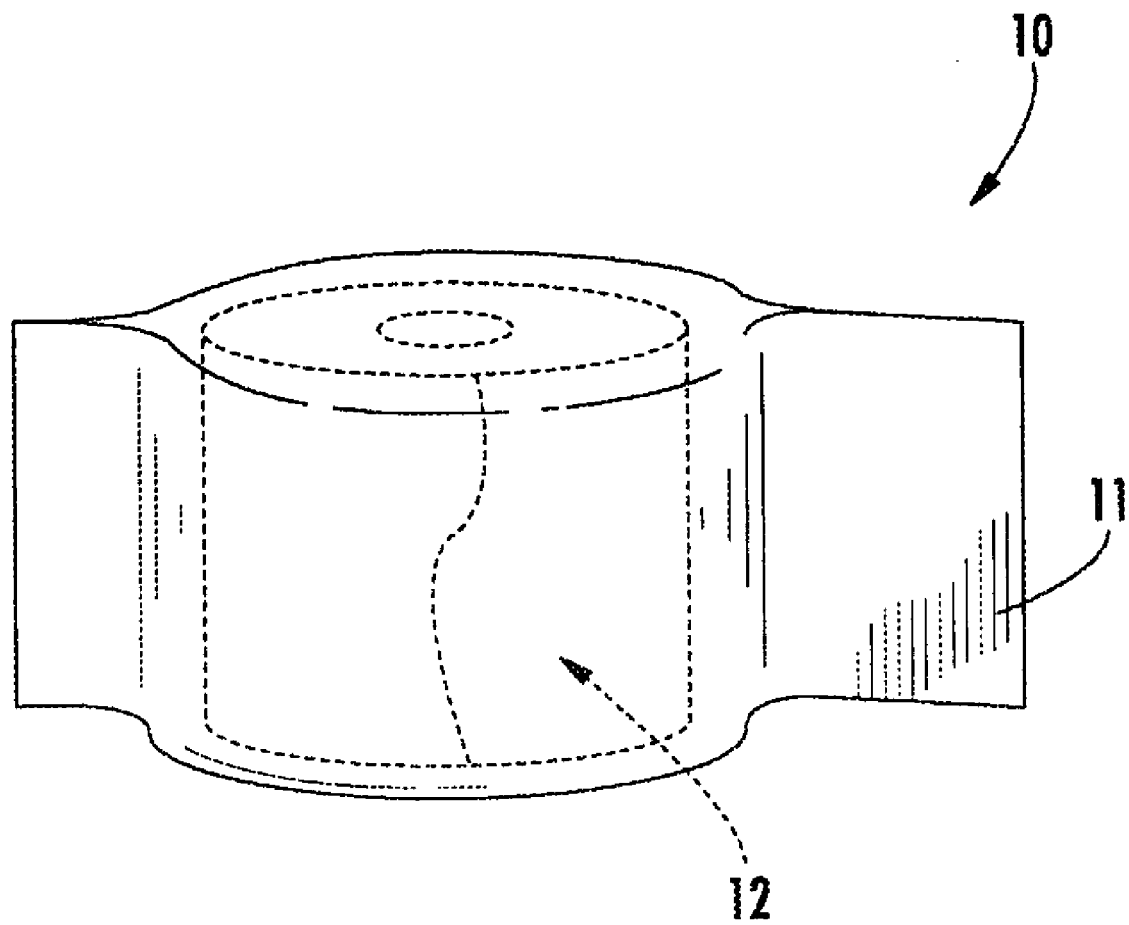
FIG. 1 is a perspective view of a cast bandage product including a moisture-proof storage package and a medical cast bandage.

Referring now specifically to the drawings, a cast bandage product according to the present invention is illustrated in FIG. 1 and shown generally at reference numeral 10. The cast bandage product 10 includes a moisture proof package, such as a pouch 11, in which is sealed a roll of flexible cast bandage 12 according to the invention. The cast bandage 12, coated or impregnated with a moisture-curable resin, is sealed in moisture-free conditions and remains in a flexible condition until the pouch is opened for use.

Figure 2:
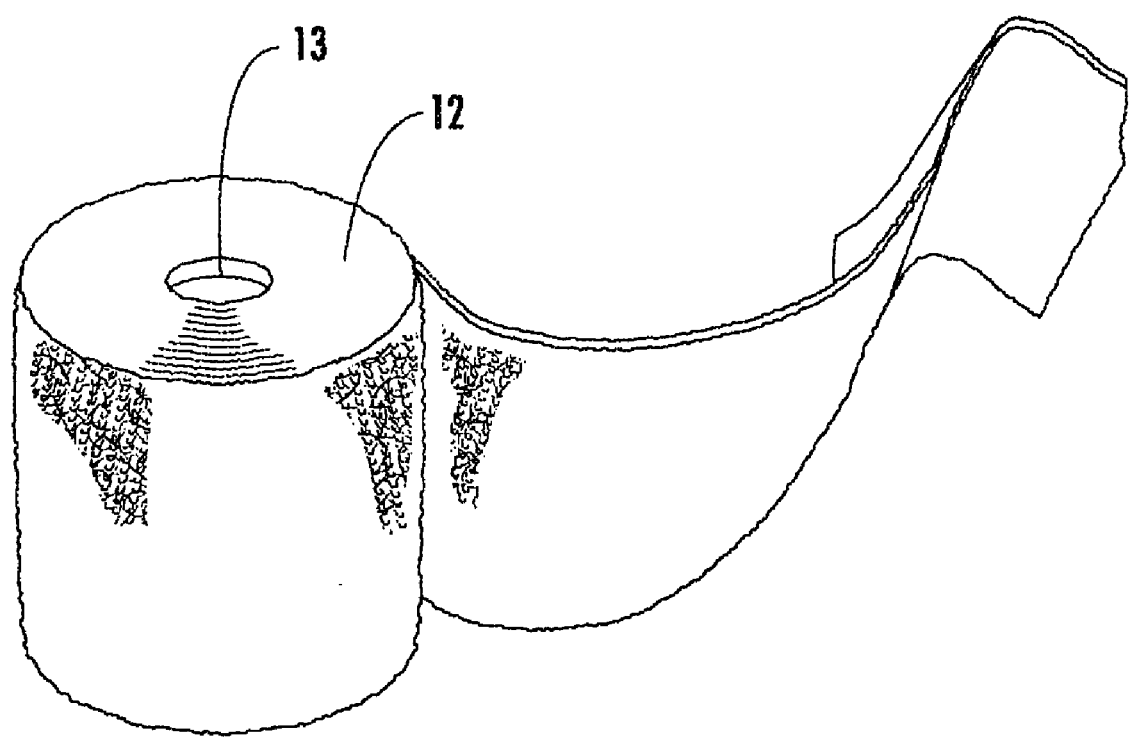
FIG. 2 is a perspective view of a soft cast bandage according to an embodiment of the invention.
Figure 3:
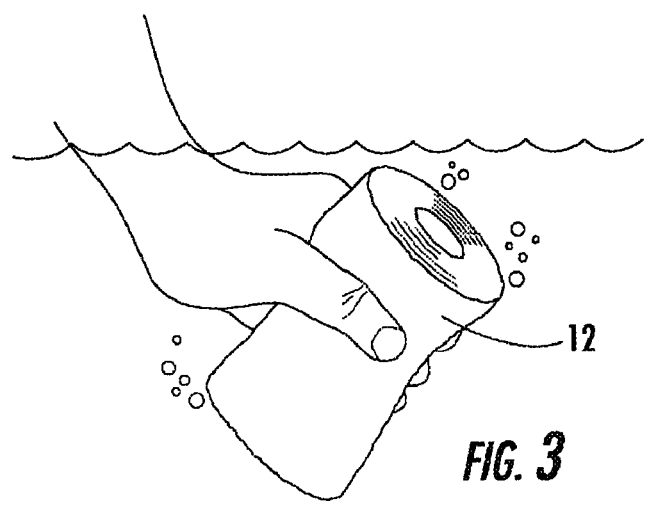
FIGS. 3-7 are sequential views of the steps by which the soft cast bandage is prepared and applied to a lower leg.
Figure 4:
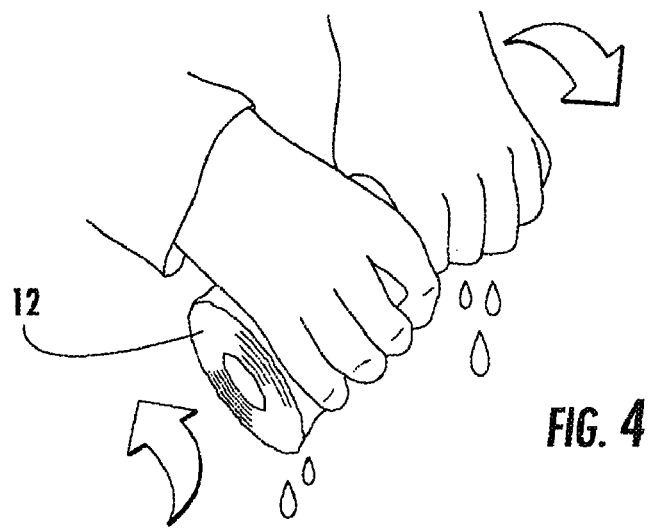
Figure 5:
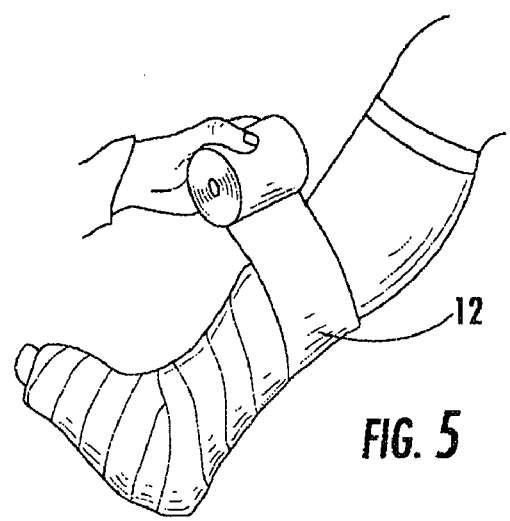
Figure 6:
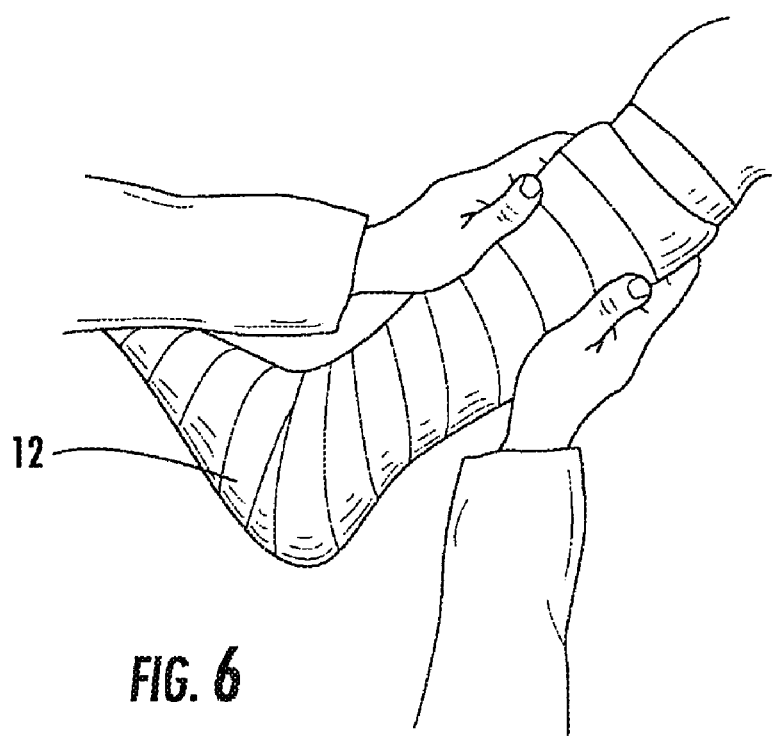
Figure 7:
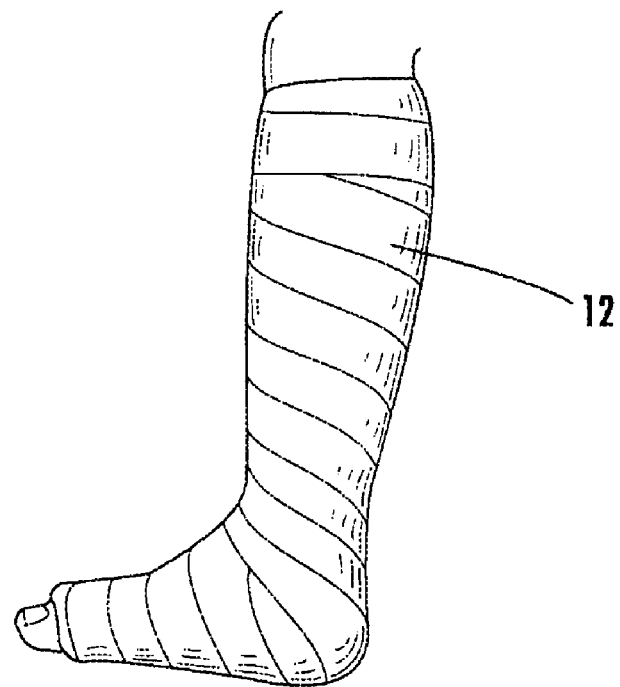
Figure 8:
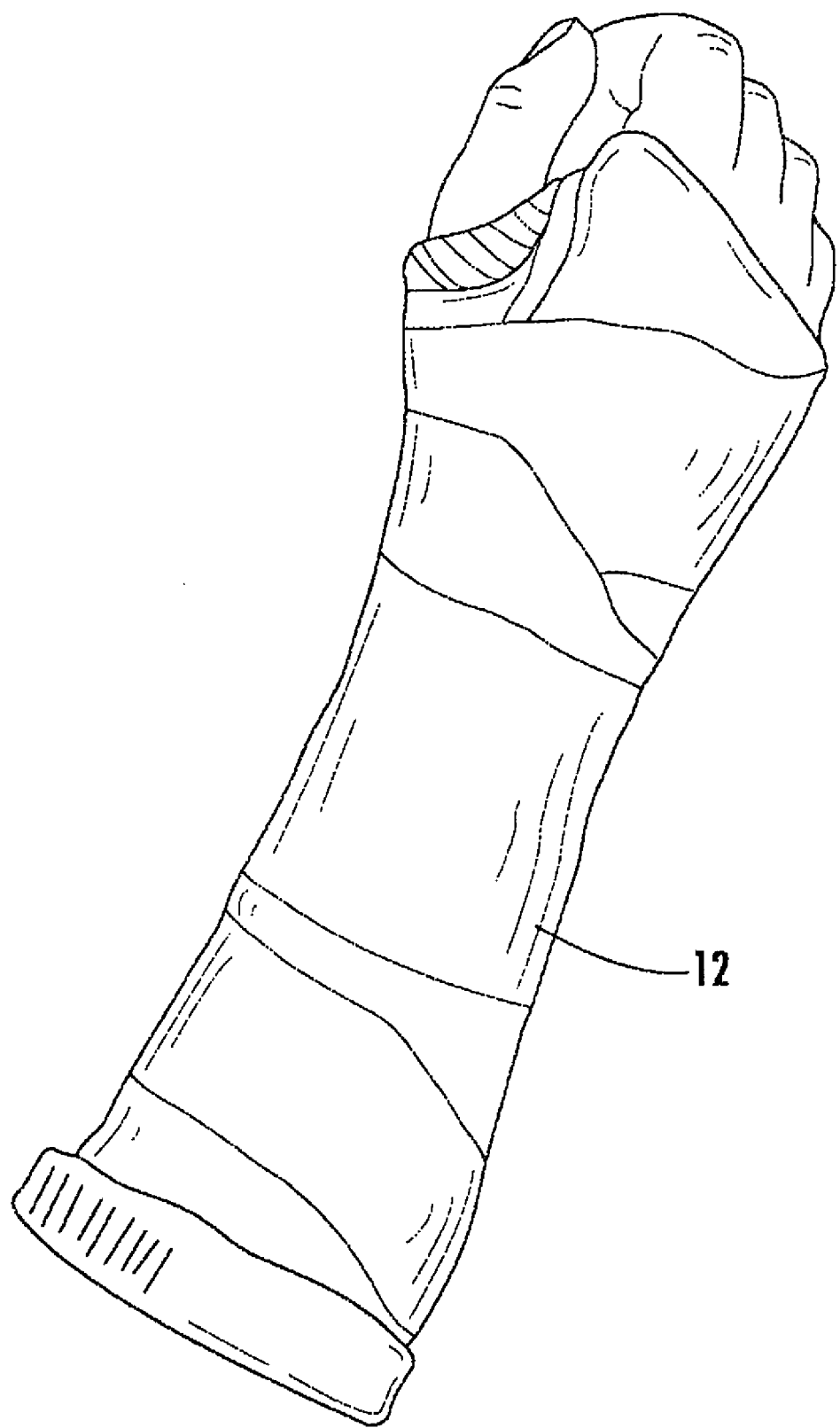
FIGS. 8 is a view of the cast bandage as applied to a forearm.

Referring now to FIG. 2, the flexible cast bandage 12 is knitted in widths from, for example, 2.5 cm (1 in.) to 12.5 cm (5 in.). The cast bandage 12 is cut into suitable lengths, for example, from 1.8 m (2 yds) to 3.6 m (4 yds.), or into suitable pre-cut shapes, for example, reinforcement slabs of 10 cm to 12.5 cm (4-5 in.) wide, and 38 cm to 75 cm (4-5 in.) long.

The cast bandage 12, as shown in FIG. 2, is rolled onto a core 13 for packaging. The core 13 prevents creasing of the bandage 12 and facilitates rapid, controlled, unrolling of the bandage during application.

The cast bandage 12, according to one preferred embodiment of the invention, is a 3 bar knitted fabric knitted on a 10E gauge Raschel knitting machine with a construction of:

Bar 1, 1-0/0-1, 3766 mm run in per rack
Bar 2, 3-3/0-0, 2682 mm run in per rack
Bar 3, 0-0/1-1, 580 mm run in per rack
All bars are fully set.

The fabric is knit at 10 courses per cm. The machine state is 45.3, relaxed 88-104.

The preferred yarn types are:
Bar 1, 470 DTex High Tenacity Polypropylene
Bar 2, 280 DTex High Tenacity Polyester
Bar 3, 70 Dtex Uncovered Elastane A preferred resin formulation is as follows:

| Component | % of Composition |
| --- | --- |
| Voranol 222-056 | 24.5 |
| Voranol 222-029 | 23.41 |
| Voranol 230-238 | 7.5 |
| Total Polyol Blend | 55.41 |
| Pluronic F108 | 1.48 |
| Irganox 1010 | 0.2 |
| Antifoam 1400 | 2.95 |
| Methane Sulphonic Acid | 0.04 |
| Mondur CD | 28.07 |
| DMDEE catalyst | 2.01 |
| Baytec 101 | 9.84 |
| Ethane Diol (increases viscosity) | As required |
|  | 100.00 |

Viscosity is 75,000 to 100,000 cps at 25 C., with an isocyanate content of 4.8 to 6.2%.

The construction and resin formulation set out above produces a soft cast bandage having a IV of between 30 and 42, dependant on the percent resin add-on.

| | Immobilization Value | | | | | | |
| --- | --- | --- | --- | --- | --- | --- | --- |
| Test # | 50 | 51 | 52 | 53 | 54 | 55 | 56 |
| 1 | 30.1 | 39.5 | 38.9 | 41.6 | 40.1 | 38.8 | 40.7 |
| 2 | 40.9 | * | * | 42.1 | 37.6 | 42.5 | 38.8 |
| 3 | 36.3 | 35.1 | 41.6 | 37.3 | 36.7 | 35.9 | 37.6 |
| Average | 35.8 | 37.3 | 40.3 | 40.3 | 38. | 39 | 39 |

*Values excluded from averages due to variation from test standard. Upon measurement, it was determined that the edges of adjacent windings were too close together.

The IV is determined by a test method that includes fabrication of a simulated limb onto which the cast bandage 12 is wrapped. The simulated limb is fabricated of Bentonite and Deionized water, as follows:

Mixing Procedure

Add 1980 gm of deionized water to a batch mixer, such as a Kitchen Aid Artisan 5 qt. mixer, or equivalent.

Set mixer on mix speed and slowly add 264 gm of Bentonite over 15 minutes.

Scrape down sides of the mixing bowl and paddle. Mix for 15 minutes on speed setting "2".

Scrape down side of the mixing bowl and paddle. Continue mixing for additional 45 minutes on speed setting "2".

Transfer the premix to container with tight lid to prevent loss of moisture and let premix stand at room temperature for 16 to 24 hours.

Store container in refrigerator at 2 to 5 C. overnight before use.

Preparation of Unwrapped Simulated Limb 816 gm Premix at 2 to 5 C. placed in mixer.

Mix for 2 minutes at mix speed.

Stop mixer and immediately introduce 174 gm of 3M Scotch-Seal Chemical Grout 5610 (Gel) into premix.

Start mixer and mix at maximum speed ("10") for 15 to 20 seconds.

Immediately remove the mixing bowl and pour mixture into a polyethylene lined cylindrical mold, 6 cm diameter, 30.5 cm long to within 1 cm of top of mold.

Allow material to cure in mold for 24 hours.

Remove simulated limb from mold and store in polyethylene storage bag at 2 to 5 C.

Wrapped Simulated Limb

Remove simulated limb from refrigerator and condition at room temperature for 2 to 4 hours.

Remove an water drops from the surface of the simulated limb with a paper towel and cover the simulated limb from end-to-end with stockinet.

Place the stockinet-covered simulated limb in a holding fixture.

A 3.6 m (4 yd.) length of cast bandage 12 is removed from its moisture proof package and immediately immersed in water at 20 C. for 20 seconds and then immediately wrapped around the simulated limb spirally to provide a total of 4 layers over a length of 23 to 25 cm, with a distance between adjacent edges of 1.9 cm (¾ in.).

The wrapped simulated limb is allowed to cure at room temperature for 1 hour.

The wrapped simulated limb is placed in a polyethylene storage bag and stored at 2 to 5 C. for 18 to 24 hours.

Measurement of Immobilization Value

A mounting fixture is provided. The fixture has a base with ¾ in. thick, half-round, vertical aluminum bars are mounted on the base. The centers of the bars are 3 in. apart. The base also includes an upper movable member of ¾ inch thick aluminum bar with a half round lower surface positioned midway between the lower bars and parallel to them.

The wrapped simulated limb is removed from the refrigerator and conditioned at room temperature for 2-4 hours.

An Instron Tensile Tester is loaded with the conditioned, wrapped simulated limb mounted on the fixture to hold the sample.

The test sample is centered on the lower member of the test fixture and perpendicular to the base supports.

The upper movable member is lowered to just contact the upper surface of the wrapped simulated limb.

The upper member is allowed to deflect the wrapped simulated limb at a rate of 2.5 cm (1 in.) per minute for 1 minute.

The force reading at the deflection point of 2.5 cm (1 in.) is taken directly from the tester and recorded as pounds of force, as the Immobilization Value "IV."

Referring now to FIGS. 3-7, the soft cast bandage 12 is applied by removing it from the storage package 11, FIG. 1, and immersing the rolled bandage 12 in cool water of about 25 C. (77 F.), FIG. 3, the technician wearing protective gloves. Excess water is wrung from the rolled bandage 12, FIG. 4, and then immediately applied to the limb in accordance with conventional application techniques, FIG. 5. The applied bandage 12 is smoothed and more closely conformed to the limb while still flexible. Upon hardening, the cast bandage is sufficiently rigid to maintain the limb in an essentially immobile position, but with enough residual softness to permit slight movement of the limb.

Softness can be controlled and varied by variation in the number of layers wrapped onto the limb and the closeness of the spiral wraps. The use of Polyester and Polypropylene yarns instead of fiberglass yarns provides significant advantages. These include greater durability, moldability, shock absorbency, and ease of removal with less dust. The cast is 100 percent radiolucent, permitting x-ray examination of the limb during treatment without removal of the cast. There are no broken glass fibers to cause dust, skin pricks and irritation, and the edges are smooth and soft.

A soft cast material is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A medical bandaging product, comprising:
   (a) a package formed of a moisture-impervious material and sealable to prevent entry of moisture;
   (b) a medical bandage positioned within the package in substantially moisture-free conditions and sealed therein against moisture until use, the medical bandage comprising:
   (i) a fabric having a pair of opposed, major surfaces; and
   (ii) a reactive system impregnated into or coated onto the fabric, the system remaining stable when maintained in substantially moisture-free conditions and hardening upon exposure to sufficient moisture to form a self supporting structure having an immobilization value of less than about 43 pounds.

2. A medical bandaging product according to claim 1, wherein the fabric comprises a knitted fabric.

3. A medical bandaging product according to claim 1, wherein the fabric comprises a knitted fabric fabricated from high tenacity polyester and high-tenacity polypropylene yarns.

4. A medical bandaging product according to claim 3, wherein the fabric includes an elastic yarn.

5. A medical bandaging product according to claim 1, 2, 3 or 4, wherein the medical bandage comprises a rolled elongate tape.

6. A medical bandaging product according to claim 1, wherein the immobilization value is between about 30 and 43 pounds.

7. A medical bandaging product according to claim 1, wherein the medical bandage is fabricated from high tenacity polypropylene, high tenacity polyester and an elastic yarn.

8. A medical bandaging product according to claim 7, wherein the high tenacity polypropylene yarn comprises 470

Dtex yarn, the high tenacity polyester yarn comprises 280 Dtex yarn and the elastic yarn comprises 70 Dtex uncovered Elastane.

9. A medical bandaging product according to claim 1, wherein the reactive system comprises a blended polyisocyanate, polyol, catalyst and stabilizer.

10. A medical bandaging product according to claim 9, wherein the polyol comprises a 55 percent by weight polyol blend.

11. A medical bandaging product according to claim 1, wherein the medical bandage has a reactive system add-on of between about 50 and 56 percent by weight.

12. A cast tape, comprising:
   (a) an elongate bandage for being positioned within a package in substantially moisture-free conditions and sealed therein against moisture until use, the bandage comprising:
      (i) a fabric having a pair of opposed, major surfaces; and
      (ii) a reactive system impregnated into or coated onto the fabric, the system remaining stable when maintained in substantially moisture-free conditions and hardening upon exposure to sufficient moisture to form a self supporting structure having an immobilization value of less than about 43.

13. A cast tape according to claim 12, wherein the fabric comprises a knitted fabric.

14. A cast tape according to claim 12, wherein the fabric comprises a knitted fabric fabricated from high tenacity polyester and high-tenacity polypropylene yarns.

15. A cast tape according to claim 14, wherein the fabric includes an elastic yarn.

16. A cast tape according to claim 12, 13, 14 or 15, wherein the cast tape is formed into a roll.

17. A cast tape according to claim 12, wherein the immobilization value is between about 30 and 43.

18. A cast tape according to claim 12, wherein the cast tape is fabricated from high tenacity polypropylene, high tenacity polyester and an elastic yarn.

19. A cast tape according to claim 18, wherein the high tenacity polypropylene yarn comprises 470 Dtex yarn, the high tenacity polyester yarn comprises 280 Dtex yarn and the elastic yarn comprises 70 Dtex uncovered Elastane.

20. A cast tape according to claim 12, wherein the reactive system comprises a blended polyisocyanate, polyol, catalyst and stabilizer.

21. A cast tape according to claim 20, wherein the polyol comprises a 55 percent by weight polyol blend.

22. A cast tape according to claim 12, wherein the medical bandage has a reactive system add-on of between about 50 and 56 percent by weight.

\* \* \* \* \*